(12) United States Patent
Hsieh et al.

(10) Patent No.: US 7,415,145 B2
(45) Date of Patent: Aug. 19, 2008

(54) METHODS AND APPARATUS FOR ARTIFACT REDUCTION

(75) Inventors: Jiang Hsieh, Brookfield, WI (US);
Stanley Haim Fox, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 798 days.

(21) Appl. No.: 10/749,033

(22) Filed: Dec. 30, 2003

(65) Prior Publication Data

US 2005/0147320 A1  Jul. 7, 2005

(51) Int. Cl.
*G06K 9/00* (2006.01)
*G06K 9/40* (2006.01)

(52) U.S. Cl. .................. 382/131; 382/261; 382/275

(58) Field of Classification Search ......... 382/131–132, 382/154, 275, 261
See application file for complete search history.

(56) References Cited

U.S. PATENT DOCUMENTS

| | | | |
|---|---|---|---|
| 4,029,963 A | 6/1977 | Alvarez et al. | |
| 5,115,394 A | 5/1992 | Walters | |
| 6,115,487 A * | 9/2000 | Toth et al. | ............. 382/131 |
| 6,266,388 B1 | 7/2001 | Hsieh | |
| 6,269,139 B1 | 7/2001 | Hsieh | |
| 6,307,909 B1 * | 10/2001 | Flohr et al. | ............. 378/4 |
| 6,373,920 B1 | 4/2002 | Hsieh | |
| 6,408,042 B1 | 6/2002 | Hsieh | |
| 6,418,189 B1 | 7/2002 | Schafer | |
| 6,421,411 B1 | 7/2002 | Hsieh | |
| 6,452,996 B1 | 9/2002 | Hsieh | |
| 6,490,333 B1 | 12/2002 | Hsieh | |
| 6,507,632 B1 | 1/2003 | Hsieh | |
| 6,600,802 B1 | 7/2003 | Hsieh | |
| 6,647,095 B2 | 11/2003 | Hsieh | |
| 6,654,440 B1 | 11/2003 | Hsieh | |
| 6,654,442 B2 | 11/2003 | Hsieh | |
| 6,678,346 B2 | 1/2004 | Hsieh | |
| 7,065,261 B1 * | 6/2006 | Horie | ............. 382/289 |
| 7,203,356 B2 * | 4/2007 | Gokturk et al. | ............. 382/154 |
| 2003/0073893 A1 | 4/2003 | Hsieh | |
| 2003/0076988 A1 * | 4/2003 | Liang et al. | ............. 382/131 |
| 2003/0128892 A1 * | 7/2003 | Avinash | ............. 382/284 |
| 2003/0185337 A1 | 10/2003 | Hsieh | |
| 2003/0185345 A1 | 10/2003 | Hsieh | |
| 2003/0223533 A1 | 12/2003 | Hsieh et al. | |
| 2004/0169658 A1 * | 9/2004 | Shin et al. | ............. 345/582 |

OTHER PUBLICATIONS

"Energy-Selective Reconstructions in X-ray Computerized Tomography," Alavarez, et al., Phys. Med. Biol., 1976, vol. 21, No. 5, 733-744.
"Dual-Kilovolt CT of Solitary Pulmonary Nodules: Importance of Equipment Calibration and Soft-Tissue Controls," Pandit-Bhalla, Radiology, Jan. 2001.
"Techniques to Alleviate the Effects of View Aliasing Artifacts in Computed Tomography," Galigekere, et al., Med. Phys. 26 (6), Jun. 1999.
"Lung Nodules: Dual-Kilovolt Peak Analysis with CT-Multicenter Study," Swensen, et al., Radiology, Jan. 2000.

* cited by examiner

*Primary Examiner*—Samir A. Ahmed
*Assistant Examiner*—Nathan Bloom
(74) *Attorney, Agent, or Firm*—Armstrong Teasdale LLP (57) ABSTRACT

A method for facilitating a reduction in image artifacts is provided. The method includes receiving data regarding a scan of an object, reconstructing a plurality of images using the received data to form a three-dimensional image space, determining an orientation for a maximum intensity pixel operation, locating the maximum intensity pixels within a plurality of ray paths in accordance with the determined orientation, and filtering around each maximum intensity pixel along each ray path.

18 Claims, 5 Drawing Sheets

METHODS AND APPARATUS FOR ARTIFACT REDUCTION

BACKGROUND OF THE INVENTION

This invention relates generally to imaging systems and more particularly to methods and apparatus for reducing image artifacts.

When performing a helical scan with a computed tomography (CT) system, the attenuation path through the scanned object can vary. Such variance or non-uniformity in the attenuation path, coupled with using less than 360-degrees of projection data in the image reconstruction process, can result in image artifacts, such as Venetian blind or zebra artifacts, in the three-dimensional reformatted image. Venetian blind artifacts appear as alternating dark and light horizontal, or parallel, bars or lines in an image.

Venetian blinds artifacts can be observed in nearly all maximum intensity projection or volume reduced images. Accordingly, methods and apparatus that facilitate the reduction of artifacts is desirable.

BRIEF SUMMARY OF THE INVENTION

In one aspect, a method for facilitating a reduction in image artifacts is provided. The method includes receiving data regarding a scan of an object, reconstructing a plurality of images using the received data to form a three-dimensional image space, determining an orientation for a maximum intensity pixel operation, locating the maximum intensity pixels within a plurality of ray paths in accordance with the determined orientation, and filtering around each maximum intensity pixel along each ray path.

In another aspect, a method for facilitating a reduction in image artifacts is provided. The method includes receiving data regarding a scan of an object, reconstructing a plurality of images using the received data to form a three-dimensional image space, determining an orientation for a maximum intensity pixel operation which is at an angle relative to a reconstructed image plane, and locating the maximum intensity pixels along a plurality of ray paths in accordance with the determined orientation.

In another aspect, a method for facilitating a reduction in image artifacts is provided. The method includes receiving data regarding a scan of an object, reconstructing a plurality of images using the received data to form a three-dimensional image space, calculating an aspect ratio by taking a ratio of an intensity of two projections of the images, and filtering based on the aspect ratio.

In yet another aspect, an imaging system is provided that includes a radiation source, a radiation detector, and a computer operationally coupled to the radiation source and the detector. The computer is configured to receive data regarding a scan of an object, reconstruct a plurality of images using the received data to form a three-dimensional image space, calculate an aspect ratio by taking a ratio of an intensity of two projections of the images, and filter based on the aspect ratio.

In yet another aspect, a computer readable medium encoded with a program configured to instruct a computer to receive data regarding a scan of an object, reconstruct a plurality of images using the received data to form a three-dimensional image space, calculate an aspect ratio by taking a ratio of an intensity of two projections of the images, and filter based on the aspect ratio.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one or more revolutions of the x-ray source and detector.

In an axial scan, the projection data is processed to reconstruct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered back projection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
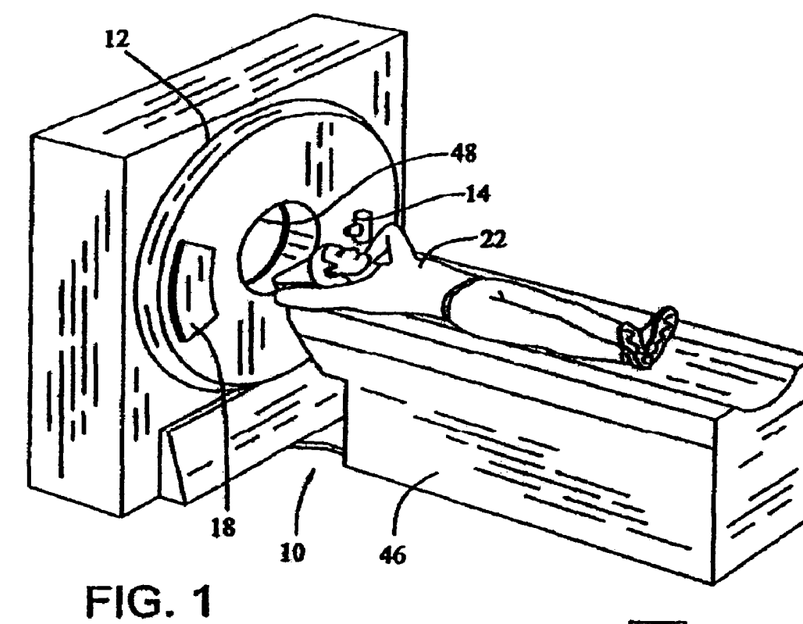
FIG. 1 is a pictorial view of a CT imaging system.
Figure 2:
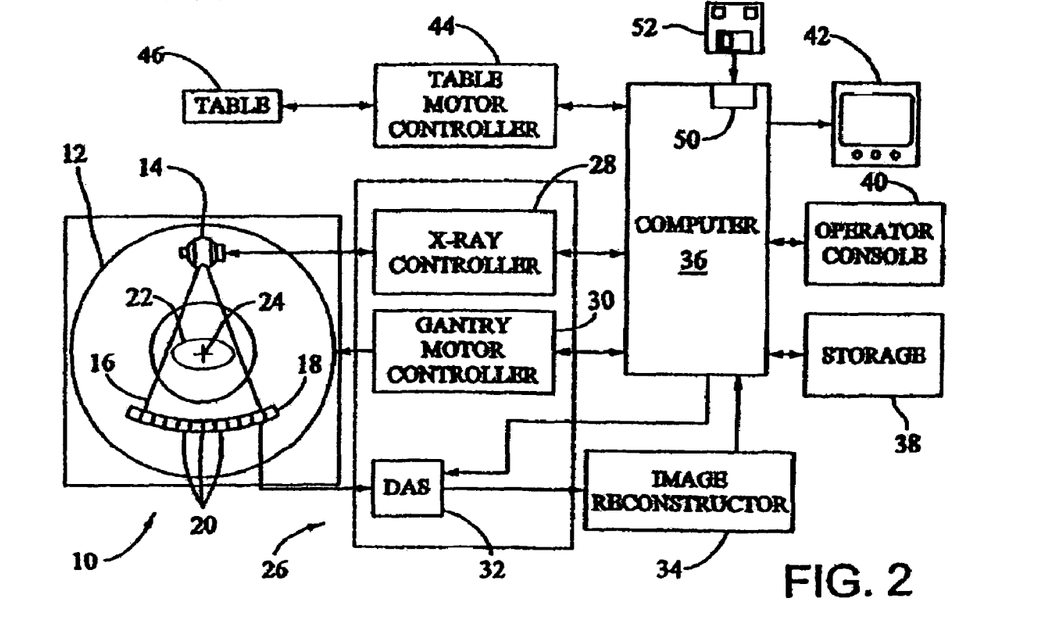
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. A collimator assembly 19 is positioned between array 18 and source 14. Collimator assembly 19 includes a known bowtie filter 21 and a bowtie addition 23. Bowtie addition 23 is fabricated from any material suitable for fabricating known bowtie filters. In one embodiment, bowtie addition 23 is positioned between bowtie filter 21 and array 18. Alternatively, addition 23 is positioned between bowtie filter 21 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as, but not limited to, a floppy disk, a CD-ROM, a DVD, a network, and/or the Internet, In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center, and that addition 23 is used for objects other than organs.

Figure 3:
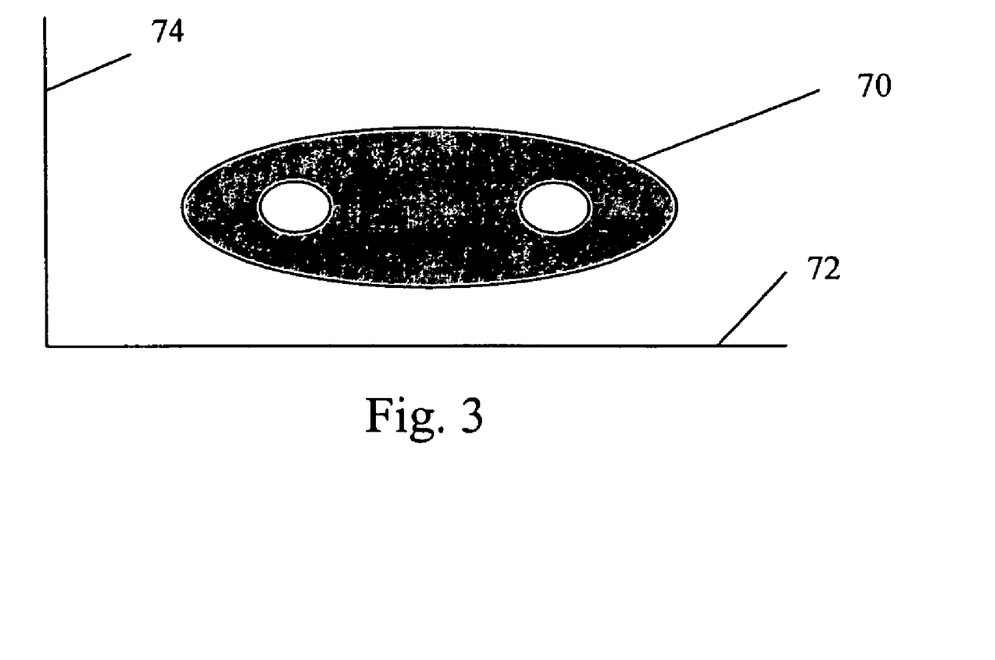
FIG. 3 is an illustration of an object that has non-uniformity of attenuation path.

Herein are described novel methods and apparatus for use in imaging systems. Generally, variation in the projection data is compensated for during data collection (e.g., via auto-mA and/or adaptive filtering, as explained in greater detail below) or post-processing techniques are utilized after the images are reconstructed (e.g., via modified MIP and/or adaptive image filtering, as explained in greater detail below). More particularly, one cause of the Venetian blind artifact is the combination of non-uniformity of noise in the projections and the less than 360-degree projection data used in the reconstruction. The non-uniformity of the projection is produced by the highly different attenuation paths of the scanned object. For example, when scanning the pelvis portion of a patient 70, the amount of attenuation in a horizontal path 72 is significantly larger than a vertical path 74, as illustrated in FIG. 3. When constant x-ray tube current is used during a scan, projections collected near the horizontal direction exhibit much worse signal-to-noise ratio (SNR) than their vertical counterpart.

For a reconstructed image, there may be a periodic noise variation from image to image, which is different from at least some known Venetian blinds artifacts in which the noise changes within each image. In general, the higher the noise level in the projection data, the larger the magnitude of the Venetian blinds artifacts. The level of image artifact can be significantly reduced or eliminated with a slow helical pitch (pitch less than 1:1). Based on the above discussion, there are several methods that can be used to reduce or eliminate Venetian blinds artifacts, as set forth below.

The non-uniform projection noise can be compensated for using true auto-mA. That is, the x-ray tube current adjusts not only as a function of z-axis position, but also as a function of projection angle. The adjustment is based on a measured average attenuation. By making the projection noise homogeneous, artifacts can be reduced or eliminated.

In addition, adaptive filtering techniques can be used to achieve an auto-mA effect. Several adaptive filtering techniques, such as specific task artifact reduction (STAR) and advanced artifact reduction (AAR) are known, and the techniques can be extended to handle the noise inhomogeneous problem and can be used for Venetian blinds artifact reduction. For example, the adaptive filtering technique is configured to increase filtering in vertical views and decrease filtering in horizontal views such that a substantially constant SNR is achieved at detector 20.

Figure 4:
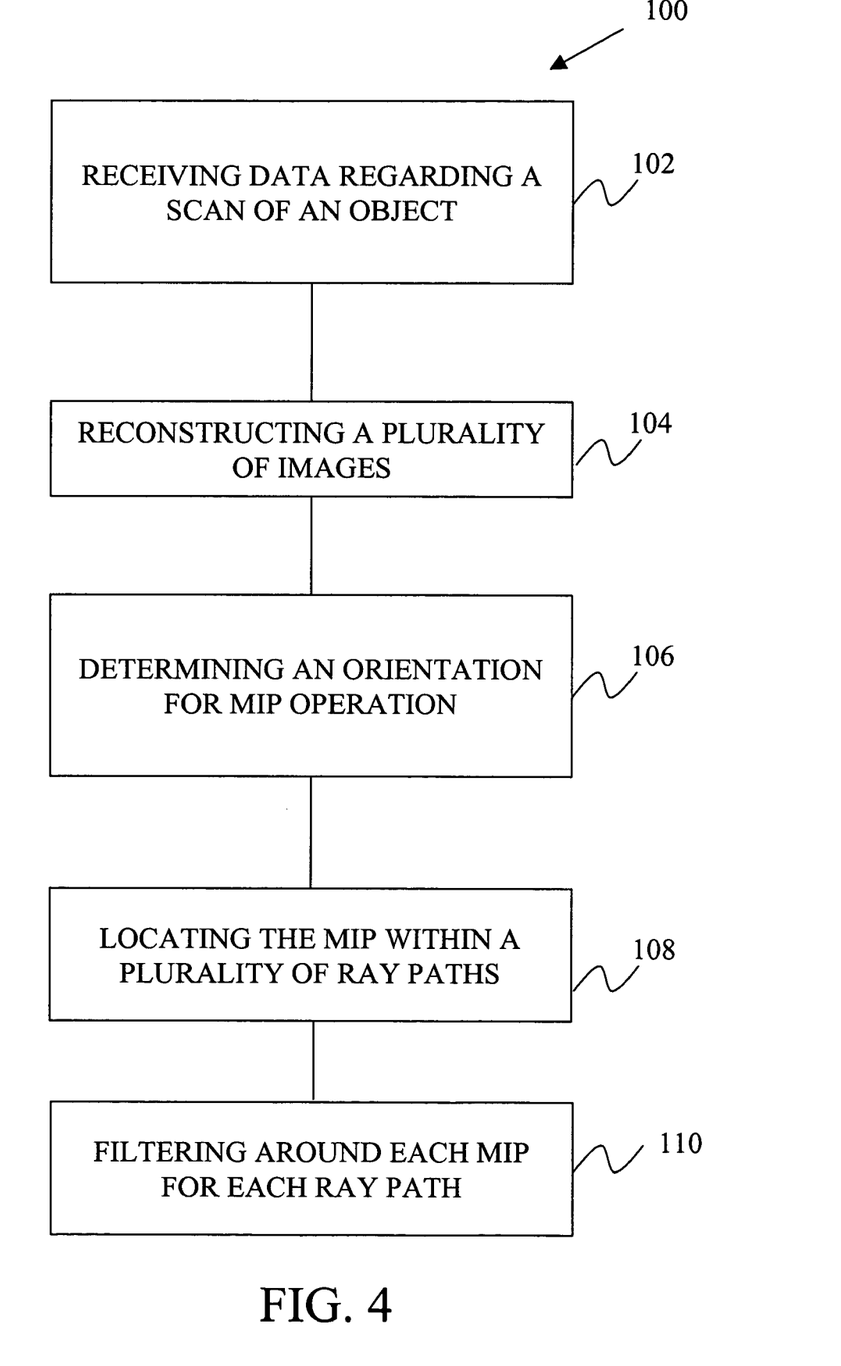
FIG. 4 is a flow diagram for reconstructing a plurality of images using the imaging system in FIG. 1.

Further, advanced maximum intensity projection (MIP) or volume rendering algorithms can be used to generate images. FIG. 4 is a flow diagram of one example of an advanced MIP or volume rendering method 100 for facilitating a reduction in image artifacts. Method 100 includes receiving 102 data regarding a scan of an object, reconstructing 104 a plurality of images using the received data to form a three-dimensional image space, determining 106 an orientation for a MIP operation, locating 108 the maximum intensity pixel within a plurality of ray paths in accordance with the determined orientation, and filtering 110 around each maximum intensity pixel along each ray path. In an alternative example of method 100, locating 108 the maximum intensity pixel includes locating the maximum intensity pixel at an angle relative to the reconstructed image plane.

For example, simple filters can be used along the projection ray directions to minimize impact on spatial resolution. Therefore, once the location of the maximum intensity for each projection ray is located, the average of adjacent or neighboring pixels along the ray path is calculated. The average is the weighted average (i.e., a low pass filter) or an adaptive average. That is, all the adjacent or neighboring samples whose intensities are within a pre-defined value from the MIP value are included in the filter. Those samples whose intensities are significantly different from the MIP value are excluded. This prevents or reduces the reduction of contrast of small structures due to the low-pass filtering. Alternatively, the filtering can be adaptive in the sense that the amount of filtering is determined based on the local noise property of the reconstructed image. If the noise level is high, more filtering is performed. When the noise is low, less filtering is performed. This will help to further reduce the impact of filtering on the MIP image contrast.

Figure 5:
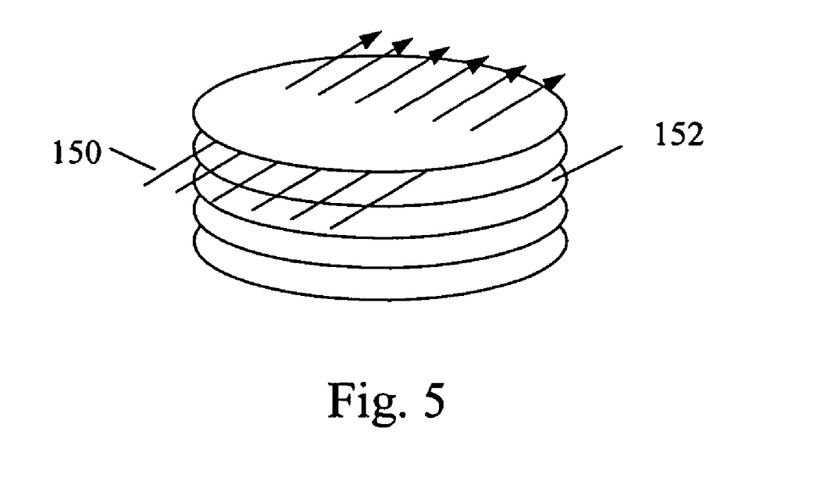
FIG. 5 is an illustration of angled production rays for a maximum intensity projection (MIP).

FIG. 5 is illustration of an alternative technique used to produce a MIP 150 at a slightly tilted angle with respect to a reconstructed image plane 152. Since the Venetian blinds artifact is caused by the noise variations from image to image, MIP calculated from several images will minimize the noise in-homogeneity.

Image space filtering techniques also can be used. Since the noise is predictable, simple image space filtering techniques can be used such that the average noise from image to image remains roughly constant. MIP or volume rendered images produced after this processing typically have minimal artifacts. An example image space filtering method using the advanced MIP methods for reconstructing images is described in details below.

Figure 6:
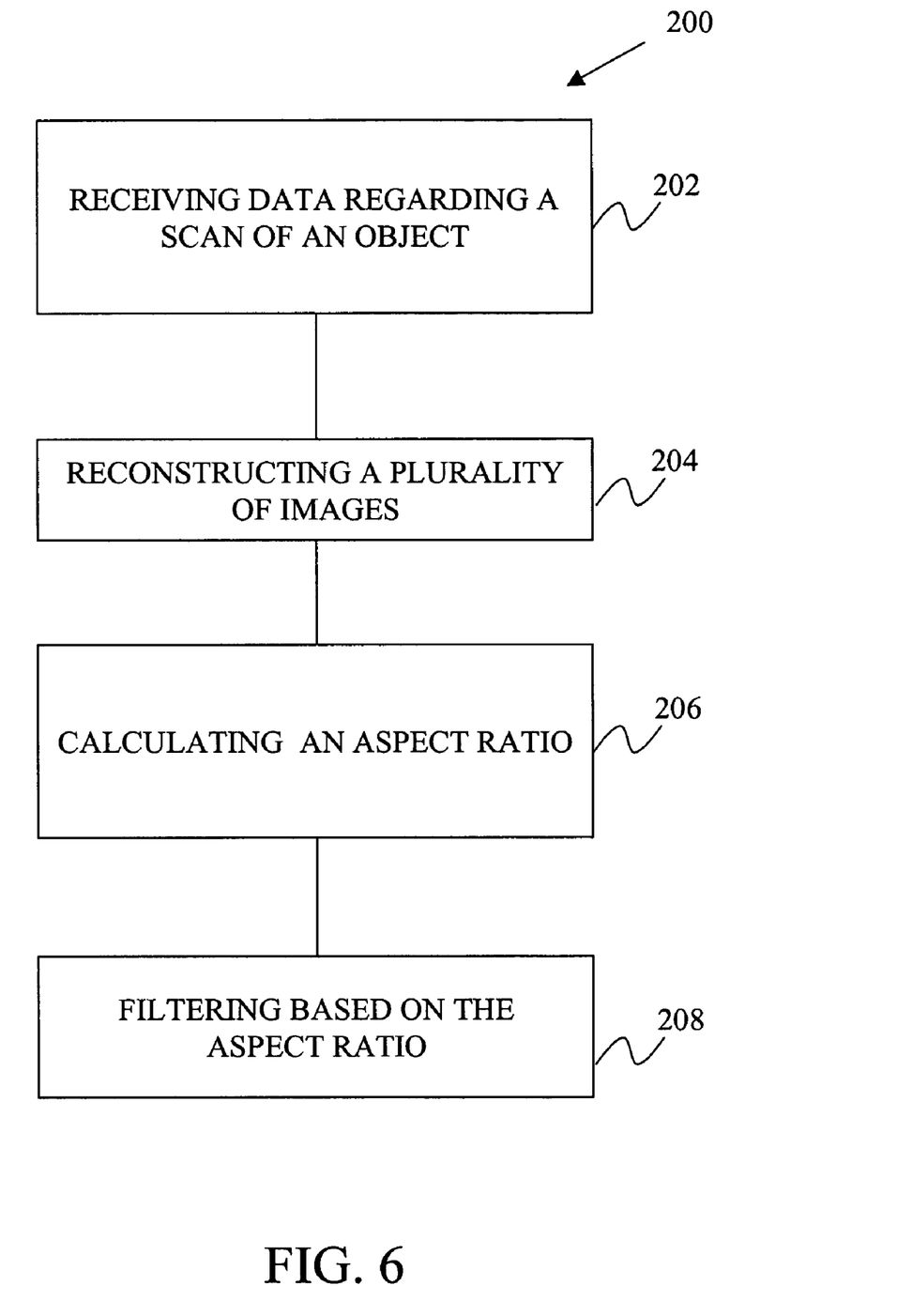
FIG. 6 is a flow diagram for reducing artifacts within images using the imaging system in FIG. 1.

FIG. 6 is a method 200 for facilitating a reduction in image artifacts. Method 200 includes receiving 202 data regarding a scan of an object, reconstructing 204 a plurality of images using the received data to form a three-dimensional image space, calculating 206 an aspect ratio by taking a ratio of an intensity of two projections of the images, and filtering 208 based on the aspect ratio.

More particularly, and for each reconstructed image from method 100, an aspect ratio of the scanned object in two orthogonal directions (e.g., horizontal and vertical directions) is determined. The aspect ratio can be calculated by taking the ratio of the intensity of the horizontal projection over the vertical projection. If the resulting ratio is less than unity, the ratio of the intensity of the vertical projection over the horizontal projection is used. The projection is calculated by summing the reconstructed images in the horizontal and vertical directions. Therefore, two one-dimensional projections are obtained from the two-dimensional image. To reduce the impact of noise, the average of the neighboring n samples around the projection samples with the maximum value are used. The ratio, r, is used partially for the determination of the noise reduction, since the higher the value of r, the more noise variation will be present in the reconstructed images from slice to slice.

Next, the object size variation along the z-direction is taken into account. This is accomplished by calculating the total mass, t, in the reconstructed image. This is obtained by summing either the horizontal or the vertical projection. Based on the total mass, a scaling function, s(t), shown in Equation 1 is calculated according to $$s(t) = \begin{cases} 1, & t \geq t_h \\ \dfrac{t - t_l}{t_h - t_l}, & t_l \leq t < t_h \\ 0 & t < t_l \end{cases} \quad (1)$$

where $t_h$ and $t_l$ are parameters. In one embodiment, $t_l$=60 and $t_h$=240. The amount of filtering is then determined by the product of r and s(t). Therefore, for each reconstructed image, I(x, y), a smoothed image, F(x, y), is calculated. Any noise reduction filter can be used (for example, a box-car filter, a Gaussian filter, or adaptive edge preserving filter). The final image, I'(x, y) is the weighted sum of the original image with the filtered image shown in Equation 2

$$I'(x, y) = k \cdot r \cdot s(t) \cdot F(x, y) + [1 - k \cdot r \cdot s(t)] I(x, y) \quad (2)$$

where k is a scaling factor. In one embodiment, k=0.2.

Figure 7:
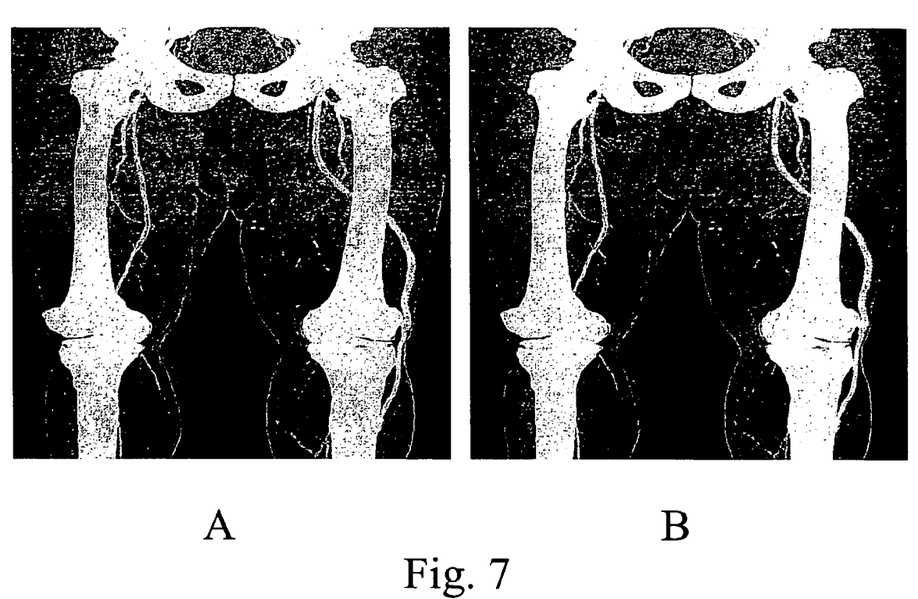
FIG. 7 is an illustration of patient MIP images.

FIG. 7 is an illustration of patient MIP images without (a) the herein described filtering and with (b) the herein described projection noise filtering scheme. Venetian blinds image artifacts are more discernible in image (a) and less discernible in image (b), thus reducing projection noise substantially reduces Venetian blinds image artifacts.

Exemplary embodiments are described above in detail. At least one technical effect of the invention is reducing projection noise, thereby substantially reducing Venetian blinds image artifacts, which is an image quality issues for multi-slice helical CT scans. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method for facilitating a reduction in image artifacts, said method comprising:
   receiving data regarding a scan of an object;
   reconstructing a plurality of images using the received data to form a three-dimensional image space;
   calculating a horizontal projection of the image by summing the reconstructed images in the horizontal direction;
   calculating a vertical projection of the image by summing the reconstructed images in the vertical direction;
   calculating an aspect ratio by taking a ratio of an intensity of the horizontal projection and the vertical projection; and
   filtering based on the aspect ratio.

2. A method in accordance with claim 1 wherein said calculating an aspect ratio comprises calculating the ratio of the intensity of the horizontal projection over the vertical projection.

3. A method in accordance with claim 2 wherein said calculating the ratio of the intensity of the horizontal projection over the vertical projection comprises locating and averaging a plurality of maximum projection samples.

4. A method in accordance with claim 1 further comprising determining a scaling function using $$s(t) = \begin{cases} 1, & t \geq t_h \\ \dfrac{t - t_l}{t_h - t_l}, & t_l \leq t < t_h \\ 0 & t < t_l \end{cases}$$

where:
t is the total mass in the reconstructed image calculated by at least one of the horizontal projection and the vertical projection; and
$t_h$ and $t_l$ are parameters.

5. A method in accordance with claim 1 further comprises determining a smoothed image from the reconstructed image.

6. A method in accordance with claim 1 further comprises determining a final image using $$I'(x, y) = k \cdot r \cdot s(t) \cdot F(x, y) + [1 - k \cdot r \cdot s(t)]I(x, y)$$

where:
k is a scaling factor;
r is an aspect ratio;
s(t) is the scaling function;
F(x,y) is a smoothed image;
I(x,y) is a reconstructed image; and
I'(x,y) is a final image, the final image is the weighted sum of the original image with the filtered image.

7. An imaging system comprising:
   a radiation source;
   a radiation detector; and
   a computer operationally coupled to said radiation source and said detector, said computer configured to:
   receive data regarding a scan of an object;
   reconstruct a plurality of images using the received data to form a three-dimensional image space;
   calculating a horizontal projection of the image by summing the reconstructed images in the horizontal direction;
   calculating a vertical projection of the image by summing the reconstructed images in the vertical direction;
   calculate an aspect ratio by taking a ratio of an intensity of the horizontal projection and the vertical projection; and
   filter based on the aspect ratio.

8. An imaging system in accordance with claim 7 wherein to calculate an aspect ratio said computer is further configured to calculate the ratio of the intensity of the horizontal projection over the vertical projection.

9. An imaging system in accordance with claim 7 wherein to calculate the ratio of the intensity of the horizontal projection over the vertical projection said computer is further configured to locate and to average a plurality of maximum projection samples.

10. An imaging system in accordance with claim 7 wherein said computer is further configured to determine a scaling function using $$s(t) = \begin{cases} 1, & t \geq t_h \\ \dfrac{t - t_l}{t_h - t_l}, & t_l \leq t < t_h \\ 0 & t < t_l \end{cases}$$

where:
t is the total mass in the reconstructed image calculated by at least one of the horizontal projection and the vertical projection; and
$t_h$ and $t_l$ are parameters.

11. An imaging system in accordance with claim 7 wherein said computer is further configured to determine a smoothed image from the reconstructed image.

12. An imaging system in accordance with claim 7 wherein said computer is further configured to determine a final image using $$I'(x, y) = k \cdot r \cdot s(t) \cdot F(x, y) + [1 - k \cdot r \cdot s(t)]I(x, y)$$

where:
k is a scaling factor;
r is an aspect ratio;
s(t) is a scaling function;
F(x,y) is a smoothed image;
I(x,y) is a reconstructed image; and
I'(x,y) is a final image, wherein the final image is the weighted sum of the original image with the filtered image.

13. A computer readable storage medium encoded with a program configured to instruct a computer to:
   receive data regarding a scan of an object;
   reconstruct a plurality of images using the received data to form a three-dimensional image space;
   calculate a horizontal projection of the image by summing the reconstructed images in the horizontal direction;
   calculate a vertical projection of the image by summing the reconstructed images in the vertical direction;
   calculate an aspect ratio by taking a ratio of an intensity of the horizontal projection and the vertical projection; and
   filter based on the aspect ratio.

14. A computer readable medium in accordance with claim 13 wherein to calculate an aspect ratio said program is further configured to calculate the ratio of the intensity of the horizontal projection over the vertical projection.

15. A computer readable medium in accordance with claim 13 wherein to calculate the ratio of the intensity of the horizontal projection over the vertical projection said program is further configured to locate and to average a plurality of maximum projection samples.

16. A computer readable medium in accordance with claim 13 wherein said program is further configured to determine a scaling function using $$s(t) = \begin{cases} 1, & t \geq t_h \\ \dfrac{t - t_l}{t_h - t_l}, & t_l \leq t < t_h \\ 0 & t < t_l \end{cases}$$

where:
t is the total mass in the reconstructed image calculated by at least one of the horizontal projection and the vertical projection; and
$t_h$ and $t_l$ are parameters.

17. A computer readable medium in accordance with claim 13 wherein said program is further configured to determine a smoothed image from the reconstructed image.

18. A computer readable medium in accordance with claim 13 wherein said program is further configured to determine a final image using $$I'(x, y) = k \cdot r \cdot s(t) \cdot F(x, y) + [1 - k \cdot r \cdot s(t)] I(x, y)$$

where:
k is a scaling factor;
r is an aspect ratio;
s(t) is the scaling function;
F(x,y) is a smoothed image;
I(x,y) is a reconstructed image; and
I'(x,y) is a final image, the final image is the weighted sum of the original image with the filtered image.

* * * * *